United States Patent [19]
Monetti et al.

[11] Patent Number: 6,030,397
[45] Date of Patent: Feb. 29, 2000

[54] MINIATURIZED MEDICAL BRUSH

[75] Inventors: Richard R. Monetti, San Clemente; Robert A. Pecor, Aliso Viejo; Thomas R. Sternweiler, Laguna Nigel; Brian M. Strauss, Trabuca Canyon, all of Calif.

[73] Assignee: Micro Therapeutics, Inc., Irvine, Calif.

[21] Appl. No.: 09/217,785

[22] Filed: Dec. 21, 1998

[51] Int. Cl.$^7$ .................................................. A61B 17/00
[52] U.S. Cl. ............................................ 606/159; 606/170
[58] Field of Search .................................. 604/22, 49, 52, 604/53, 264, 280; 606/1, 159, 170

[56] References Cited

U.S. PATENT DOCUMENTS

| | | |
|---|---|---|
| 2,712,823 | 7/1955 | Kurtin . |
| 3,613,664 | 10/1971 | Willson . |
| 4,108,162 | 8/1978 | Chikashige et al. . |
| 4,227,537 | 10/1980 | Suciu et al. . |
| 4,772,258 | 9/1988 | Marangoni et al. . |
| 4,966,162 | 10/1990 | Wany . |
| 5,009,659 | 4/1991 | Hamlin et al. . |
| 5,195,954 | 3/1993 | Schnep-Pesch et al. . |
| 5,201,323 | 4/1993 | Vermeulen . |
| 5,370,653 | 12/1994 | Cragg . |
| 5,456,265 | 10/1995 | Yim . |
| 5,681,335 | 10/1997 | Serra et al. . |
| 5,882,329 | 3/1999 | Patterson et al. ........................ 606/159 |

FOREIGN PATENT DOCUMENTS 3921071 2/1991 Germany .

OTHER PUBLICATIONS

Crispin, H. A., "Die Gefaβburste—ein mit Hilfe der Gefaβbendoskopie entwickeltes neues Instrument" *Chirurg* 45:400–401 (1974).

Richie, J. L. et al., "Rotational approaches to atherectomy and thrombectomy", *Z. Kardiol.* 76:Suppl. 6, 59–65 (1987).

Cragg, Andrew H., "The Thrombolytic Brush", presented at *The Second Mid–Atlantic Conference on Angio Access: Establishment and Maintenance of Dialysis and Venous Access*, Williamsburg, VA (pp. 162–165 of proceedings (Oct. 1996).

"Cragg Thrombolytic Brush™ Quick Review" brochure 75047 Rev A by Micro Therapeutics, Inc. (1997).

"Cragg Thrombolytic Brush™" brochure 75050 Rev A by Micro Therapeutics, Inc. (1997).

*Primary Examiner*—Michael Buiz
*Assistant Examiner*—William W. Lewis
*Attorney, Agent, or Firm*—Joseph F. Breimayer

[57] ABSTRACT

A miniaturized brush particularly adapted for medical use formed at the distal end of an elongated brush drive shaft having a hollow lumen formed therein for introduction over a guidewire. The brush drive shaft is enclosed in the lumen of a brush delivery catheter and other components of a brush sub-assembly adapted to deliver infusate through the catheter lumen and to be coupled to a drive motor unit for rotating the brush drive shaft and brush. The brush bristles of the distal brush are adapted to be garaged in a distal end section of the brush delivery catheter lumen during introduction through a body lumen. The brush bristles are formed of a thin sheet of rigid plastic material that is shaped to have a plurality of fringe elements extending in parallel from a mounting web. The mounting web is wound about and attached to a distal end section of the drive shaft outer circumference so that the fringe elements extend outward from the drive shaft surface and obliquely of the drive shaft axis. Preferably, proximal and distal spiral brush sections are formed in this manner so that fluids are impelled distally and proximally, respectively, between the proximal and distal brush sections as infusate is delivered.

23 Claims, 6 Drawing Sheets

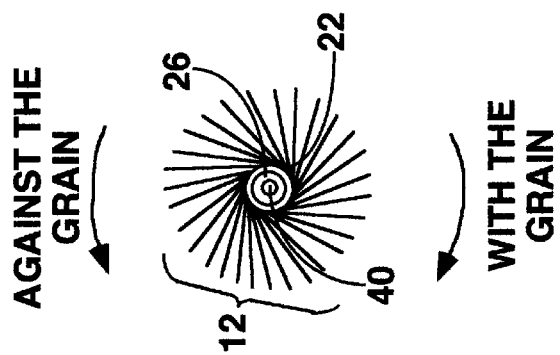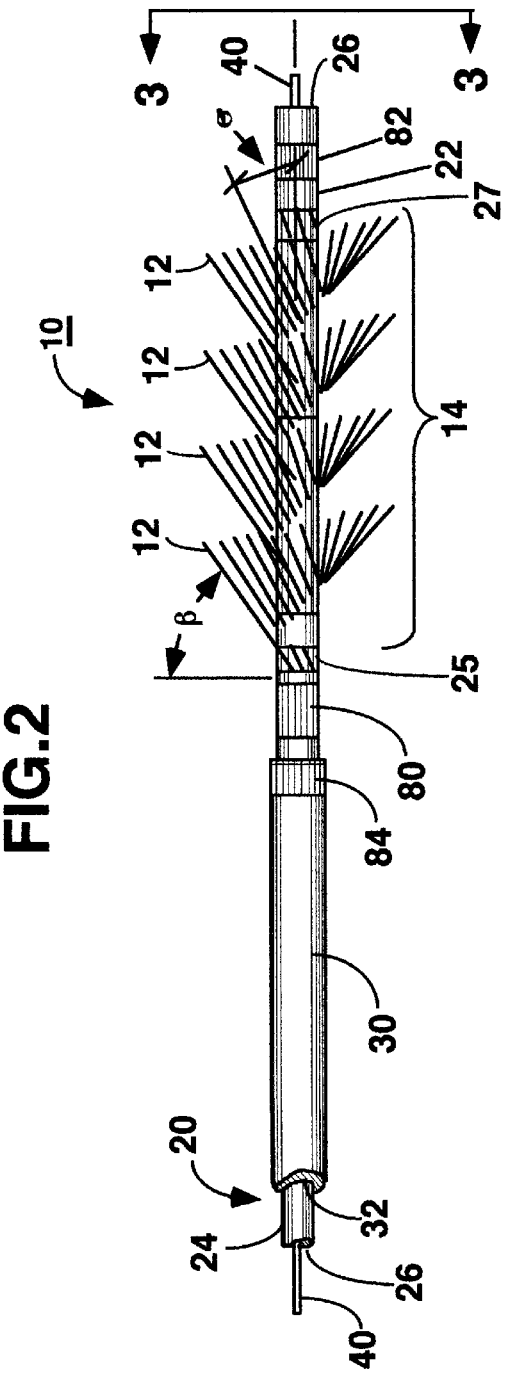

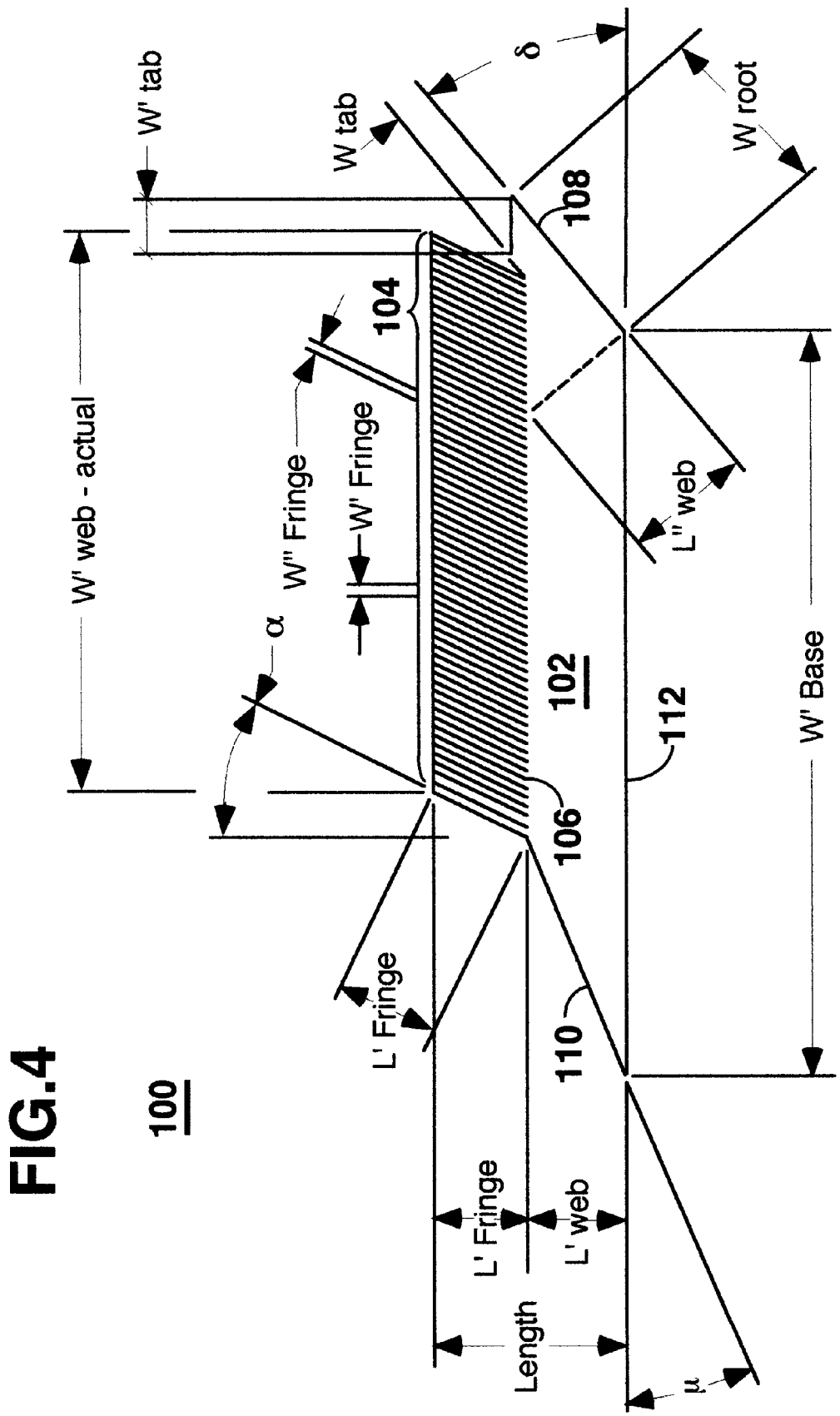

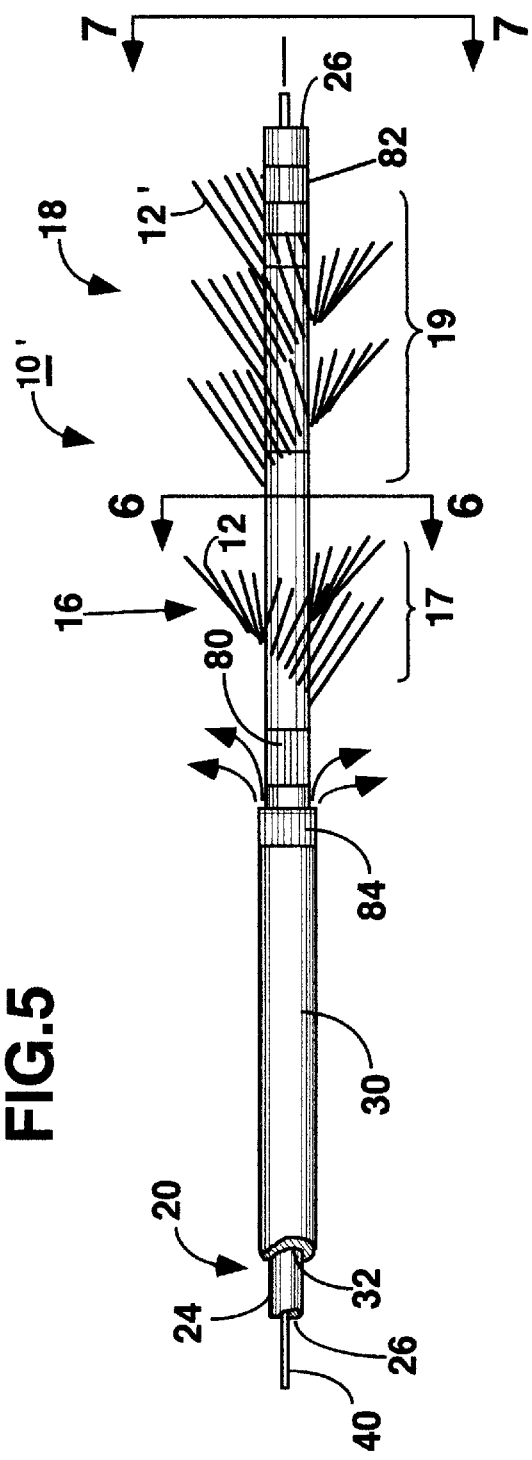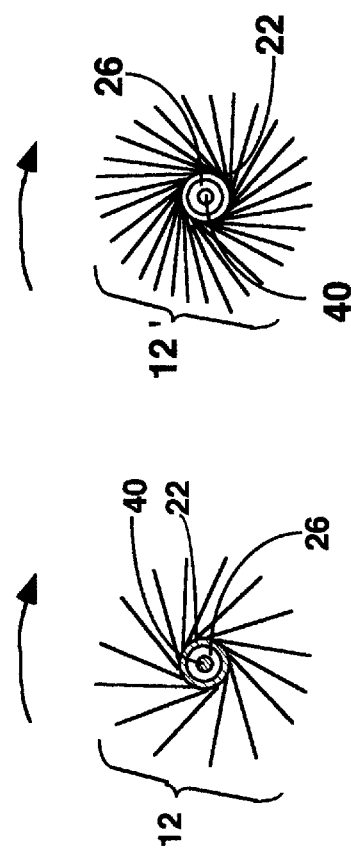

MINIATURIZED MEDICAL BRUSH

CROSS-REFERENCE TO RELATED APPLICATIONS

Reference is hereby made to commonly assigned, co-pending U.S. patent application Ser. Nos. 09/217,784, filed on even date herewith for ROTATABLE ATTACHMENT MECHANISM FOR ATTACHING A MEDICAL OBSTRUCTION TREATMENT DEVICE SUB-ASSEMBLY TO A DRIVE MOTOR UNIT in the names of Brian M. Strauss et al. and 09/217,786 filed on even date herewith for ROTATABLE DYNAMIC SEAL AND GUIDE FOR A MEDICAL OBSTRUCTION TREATMENT DEVICE SUB-ASSEMBLY COUPLED TO A DRIVE MOTOR UNIT in the names of Blair D. Walker et al.

BACKGROUND OF THE INVENTION

1. Field of the Invention

The present invention relates to a miniaturized brush particularly adapted for medical use formed at the distal end of an elongated brush body having a hollow lumen formed therein and particularly to the construction, function and uses thereof.

2. Description of the Background Art

Commonly assigned, U.S. Pat. No. 5,370,653 to Cragg, incorporated herein by reference in its entirety, discloses a thrombectomy system for dissolving a soft fibrinous obstruction, such as a recently formed thrombus, within a patient's vascular system, either in a patent vein or artery or in a vascular implant, e.g. an A/V graft. The thrombectomy system employs rotating brush bristles within the thrombus to separate the fibrin of the thrombus from blood cells while mixing the separated fibrin with a dissolving or thrombolytic agent, e.g. streptokinase or urokinase, that is introduced at the same time into the separated fibrin.

The inventive rotating brush described in the '653 patent has flexible brush bristles extending outward from a brush shaft or drive shaft distal end in all directions. The brush is attached to the elongated, flexible, rotatable drive shaft or brush shaft which is attached at its proximal end to a drive motor to impart rotary motion to the brush shaft and bristles. The system includes a brush delivery catheter adapted to be introduced and advanced through a patient's blood vessels until the distal end is positioned adjacent the soft fibrinous thrombus. Once the brush delivery catheter is positioned, the brush bristles and brush shaft are passed through the brush delivery catheter lumen and out its distal opening to place the brush in contact with the soft thrombus. The bristles are sufficiently resilient and dimensioned for allowing compression and passage out of and back into the distal opening of the introducer lumen and for mixing into and macerating the fibrin of the soft thrombus, without damaging a vessel wall.

In one embodiment, the drive shaft is solid, and the dissolving agent is introduced through the brush delivery catheter lumen alongside the drive shaft lumen while the drive shaft is rotated. The thrombolytic agent is emitted from the distal end opening of the brush delivery catheter lumen in the region of rotation of the brush bristles for dissolving the soft thrombus exposed by the rotating brush bristles.

In another embodiment described in the '653 patent, the brush shaft is hollow to define a brush shaft lumen and preferably is formed with a penetrable distal tip valve normally closing the distal end opening of the brush shaft lumen. The thrombolytic agent is optionally delivered through the brush shaft lumen and through side exit holes or ports into the region of the brush bristles. The brush shaft lumen allows the introduction of the brush over a previously introduced and positioned guidewire so that the brush may be readily advanced to a thrombus in a blood vessel. Optionally, a microcatheter bearing a distal inflatable balloon or a mesh basket may be first placed in the vessel distal to the obstruction. The brush can then be introduced over the microcatheter and used while the inflated balloon or mesh basket placed distally of the brush bristles restrains the flow of fragments distally and allows the dissolving agent to complete the dissolution thereof. No particular construction of the hollow lumen drive shaft to achieve a small overall diameter is described in the '653 patent.

In German OLS DE 3921071, the use of a spiral wound brush that is rotated to wrap the fibrin of a thrombus in its bristles is described. In certain embodiments, the brush bristles are arranged in a spiral, screw pattern around either a solid core wire or a hollow tube with a lumen adapted to receive a guidewire. The brush bristles are rotated or otherwise advanced into a thrombus and then rotated to wind up the fibrin and separate it from blood cells. The particular manner of attaching the bristles to the solid core wire or hollow tube brush shaft is not described, nor is the use of a thrombolytic agent to dissolve the thrombus suggested.

Commonly assigned U.S. Pat. No. 5,681,355 to Serra et al., incorporated herein by reference in its entirety, discloses a hollow lumen, thrombectomy brush and method of fabrication which allows for the brush to be introduced over a previously placed guidewire into a very small blood vessel. The miniaturized brush is provided with an elongated, flexible, rotatable brush or drive shaft adapted to be attached at its proximal end to a drive motor for rotating the shaft. The drive shaft is formed with a proximal elongated section formed of a hollow, thin wall tube having an inner lumen and an outer surface and a distal section. The distal section comprises a hollow, thin wall tube extension having a coiled wire wound about it entrapping brush filaments between turns of the coiled wire and the outer wall of the hollow tube extension. The brush is formed of brush filaments, each having first and second ends and a predetermined length between the first and second ends, entrapped in a winding interface between turns of the coiled wire and the outer wall of the hollow tube extension in an entrapment zone intermediate the first and second ends. The brush filaments thereby each form first and second brush bristles extending separately outward from the entrapment zone to the first and second ends thereof.

The assignee of the '653 and '355 patents and the present application has implemented the solid drive shaft brush embodiment of the '653 patent in the Cragg Thrombolytic Brush™. The Cragg Thrombolytic Brush™ is presently used in the lumen of an A/V graft implanted in a patient's vascular system for hemodialysis to dissolve thrombi that form therein. The Cragg Thrombolytic Brush™ is described and depicted in "The Thrombolytic Brush", by Andrew H. Cragg, MD presented at *The Second Mid-Atlantic Conference on Angio Access: Establishment and Maintenance of Dialysis and Venous Access,* Williamsburg, Va (pp. 162–165 of proceedings) in October 1996 and in product literature published by the assignee in 1997.

The brush and fabrication method disclosed in the '355 patent is meritorious but is expensive to produce. Moreover, the coiled wire entrapment of the brush bristles tends to make the side wall and outer diameter of the distal section larger than is desirable. This increased thickness, the angle of outward extension of the brush bristles from the entrapment zone and the stiffness of the bristles contribute to making it difficult to advance the brush through a 6 French or smaller diameter catheter lumen and out of the distal end opening thereof. A need exists for a simpler and less expensive fabrication process and resulting thrombolytic brush of this type.

SUMMARY OF THE INVENTION

It is a primary object of the present invention to provide a simplified fabrication and configuration of a medical brush that has a low profile enabling its being garaged in a small diameter guide or brush delivery catheter lumen to access a desired site in a body vessel or medical implant.

It is a principal object of the present invention to provide such a brush for use in an embolectomy procedure for removing a soft obstruction from a blood vessel or medical implant.

It is a further principal object of the present invention to ensure that the soft obstruction is completely macerated and dissolved during the rotation of the brush bristles in the soft obstruction during delivery of a thrombolytic agent.

In this regard, it is yet a further object of the present invention to provide a hollow lumen, thrombectomy brush and method of fabrication with a spiral brush configuration for macerating a thrombus and mixing infused thrombolytic agents.

Another object of the invention in this regard is to maintain the soft obstruction adjacent to the brush bristles as the spiral brush bristles are rotated and the thrombolytic agent is delivered to minimize migration of fragments of the soft obstruction within the vasculature.

It is still a further object of the invention to provide such a miniaturized brush and method of fabrication for uses in other medical applications than thrombectomy and for non-medical fields and uses where a miniaturized brush with a hollow lumen would find particular utility.

In accordance with these and other objects, a miniaturized brush sub-assembly preferably for use in thrombectomy procedures is provided with an elongated, flexible, rotatable drive shaft having a proximal elongated, drive shaft section and a distal drive shaft section in which the brush is formed. The drive shaft is adapted to be attached at its proximal end to a drive motor for rotating the drive shaft about its longitudinal axis. The brush drive shaft is preferably a hollow tube having a drive shaft lumen for receiving a guidewire for over-the-wire introduction of the drive shaft through a vascular access device lumen and into a blood vessel or vascular implant lumen. A thrombolytic agent may also be delivered from a proximal source and through the brush delivery catheter lumen alongside the drive shaft to one or more exit ports adjacent to the brush.

The brush is preferably formed of a planar sheet of thin, relatively rigid, plastic material that is shaped with an elongated mounting web having a web length and width and with a plurality of fringe elements extending at a fringe angle from one side edge of the mounting web. The fringe elements extend in parallel to one another from the side edge of the mounting web like the teeth of a comb or the separable barbs of a vane of a feather. The length of the mounting web preferably exceeds the circumference of the drive shaft distal section so that the fringe elements form a spiral winding of outwardly extending brush bristles when the mounting web is wound around the circumference.

To assemble the brush, one major surface of the mounting web is spiral wound about the exterior surface of the distal section of the drive shaft in a substantially non-overlapping manner. The ends of the mounting web are attached to the exterior surface of the distal section of the drive shaft. The brush bristles extend in a spiral pattern around the circumference tracking the winding pitch of the mounting web which is dependent upon the width of the mounting web. The length and width of the mounting web and circumference of the drive shaft distal section dictate the number of spiral revolutions of the spiral winding of brush bristles in the brush.

The fringe elements extend away from the mounting web at projection and offset angles that are related to the winding pitch, the fringe angle of the fringe elements to the mounting web and the width of the mounting web wound about the exterior wall of the brush drive shaft. After the mounting web is spiral wound about the exterior surface of the tubular drive shaft, each fringe element extends, when viewed from the side, at a projection angle away from the longitudinal axis of the drive shaft to its free end as a brush bristle. The adjacent brush bristles also spread apart from one another and extend radially away from their attached ends where they join the mounting web, when viewed from the end or in a cross-section view.

The mounting web can also be spiral wound with the brush bristles extending generally either proximally or distally. In accordance with the present invention, the brush bristles preferably extend generally distally so that they can be drawn proximally into the lumen of the brush delivery catheter and garaged there during introduction and retraction of the brush sub-assembly through the vascular system. In either case, the mounting web can also be spiral wound in a clockwise or counter-clockwise direction around the exterior surface of the drive shaft. The drive shaft can be rotated in either direction.

In each embodiment, when the drive shaft is rotated in a "with the grain" direction, the fringe element free ends are pressed inward toward the exterior surface if they contact resistance. Similarly, when the drive shaft is rotated in an "against the grain" direction, the brush bristles are bent so that the free ends extend outward and away from the exterior surface if they contact resistance. Stated another way, the brush bristles are either bent "with the grain" or "against the grain" when the drive shaft is rotated in a given direction with respect to a given winding direction. The brush bristles rotated "with the grain" are more flexible than the brush bristles rotated "against the grain".

In a first embodiment, a single such spiral winding of brush bristles is formed extending through at least one revolution about the outer surface of a distal section of the rotatable drive shaft. In use of this single spiral brush embodiment, the drive shaft and brush are advanced within an outer brush delivery catheter lumen and over a previously placed guidewire that extends through the soft obstruction. The brush is advanced into the soft obstruction and then extended out of the brush delivery catheter lumen distal end opening. The drive shaft can be rotated in either direction but is preferably rotated in the "against the grain" direction to macerate the soft obstruction. At the same time, the thrombolytic agent is applied to the soft obstruction.

In a further preferred embodiment, the brush is formed along the distal drive shaft section with a proximal spiral brush section and a distal spiral brush section each formed and attached to the distal section of the drive shaft as described above. The brush bristles of the proximal spiral brush section extend outward of the rotatable drive shaft in a spiral that moves proximal to distal in a clockwise direction when viewed from the distal end of the drive shaft. The brush bristles of the proximal spiral brush section extend preferably through at least one revolution around the circumference of the rotatable drive shaft. The brush bristles of the distal spiral brush section extend outward of the rotatable drive shaft in a spiral that moves distal to proximal in a clockwise direction when viewed from the distal end of the drive shaft. Preferably, the bristles of the distal spiral brush section also extend through at least one revolution around the circumference of the rotatable drive shaft.

The proximal and distal winding directions of the proximal and distal brush sections specified above are chosen to impel fluids distally and proximally, respectively, in the manner of opposed Archimedian screws. The brush bristles extend generally distally in both cases, but the mounting webs are wound in opposed winding directions. The proximal brush section is wound so that the brush bristles are rotated "against the grain", and the distal brush section is wound so that the brush bristles are rotated "with the grain" when the drive shaft is rotated.

The number of revolutions of the proximal and distal spiral windings and the number of bristles in each such section may be the same or differ from one another. The proximal and distal winding pitches may also be the same or differ from one another. In addition, the fringe elements of each such section may differ in number and be dimensioned differently so that the quantity and spacing of the resulting bristles differs in each section.

In the practice of the second preferred embodiment, the brush is garaged within a distal end section of the brush delivery catheter lumen, and both are advanced over the guidewire to the site. The brush is advanced out of the outer brush delivery catheter lumen and positioned in relation to a distal end of an elongated soft obstruction. The drive shaft is rotated by the proximal drive motor in a prescribed rotation direction, and the brush is retracted proximally through the soft obstruction as thrombolytic agent is delivered. The soft obstruction is macerated into particles that are trapped by the opposed fluid flow caused by the rotation of the proximal and distal spiral brush sections. The proximal brush bristles more aggressively bite into fresh portions of the soft obstruction during the rotation because they are rotated "against the grain". The distal brush bristles then continue the maceration and maintain the thrombin fragments between the proximal and distal brush sections mixing with the thrombolytic agent.

In these embodiments, the brush bristles extend distally when unrestrained to allow the brush to be readily retracted and garaged within the brush delivery catheter lumen adjacent to its distal end opening. The brush bristles formed in this manner are very thin in cross-section and can readily fold down and into a small diameter brush delivery catheter lumen for garaging during advancement and withdrawal of the brush. The fringe elements have inherent resilience that causes them to spring back to the acute fringe angle when they are released from the constraint of the lumen of the brush delivery catheter. The brush bristles spring back to their unrestrained shape to effectively mix into the fibrin of the soft obstruction yet not damage the vessel wall. The brush bristles can be selectively retracted into or extended out of the distal end opening of the brush delivery catheter lumen and into contact with a thrombus to limit or expand the maceration contact area.

The miniaturized brushes of the present invention provide reduced overall outer diameter that enables its introduction through small diameter brush delivery catheter and/or blood vessel lumens. In addition, the thin wall construction provides a drive shaft or brush body lumen with a relatively enlarged inner diameter for introduction over a guidewire and for introduction and passage of fluids therethrough. The drive shaft or brush body in each assembly is reinforced sufficiently to allow advancement through tortuous blood vessel passageways and to provide torque transfer to the distal brush.

The brushes of the present invention are also relatively easy to fabricate and attach to the distal drive shaft section and to tailor for specific applications. The characteristics of operation of the brushes can be selected by appropriately dimensioning the fringe elements and mounting web. These dimensions may be selected to determine the number of brush bristles, the spacing between adjacent brush bristles, the pitch of the spiral winding and the number of revolutions of the spiral winding and the overall length of the brush. In all embodiments and variations, the brush filaments may be trimmed to an even length or an uneven length in a desired pattern to provide flexible bristles extending outward from the drive shaft distal end.

This summary of the invention and the objects, advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other objects, advantages and features of the invention will become apparent from the following detailed description of the preferred embodiments of the invention, in which:

FIG. 2 is an enlarged, plan view of a first embodiment of the brush usable in the brush sub-assembly and drive motor unit of FIG. 1;

FIG. 3 is an end view of the brush of FIG. 2;

FIG. 4 is a plan view of a sheet of material cut to form an integral mounting web and a plurality of fringe elements;

FIG. 5 is an enlarged, plan view of a second embodiment of the brush that is also illustrated in FIG. 1 having oppositely wound proximal and distal brush sections;

FIG. 6 is an enlarged end cross-section view along lines 6—6 of the proximal brush section of FIG. 5;

FIG. 7 is an enlarged end view along lines 7—7 of the distal brush section of FIG. 5;

DETAILED DESCRIPTION OF THE PREFERRED EMBODIMENTS OF THE INVENTION

In view of the apparent interchangeable use in the background art, only the terms "soft obstruction" or "thrombus" and "thrombectomy" will be employed in the following description of the invention and the claims, and it will be understood that these terms shall embrace and be the equivalent of blood clot or embolus and embolectomy, respectively, and are applicable to the removal of soft, recently formed thrombi or blood clots. In the following description, the alternative preferred embodiments share common features of the invention which are illustrated in preferred uses described in the above-incorporated '653 patent. Other uses will be apparent from the following description of the construction of the miniaturized brushes of the present invention.

Figure 1:
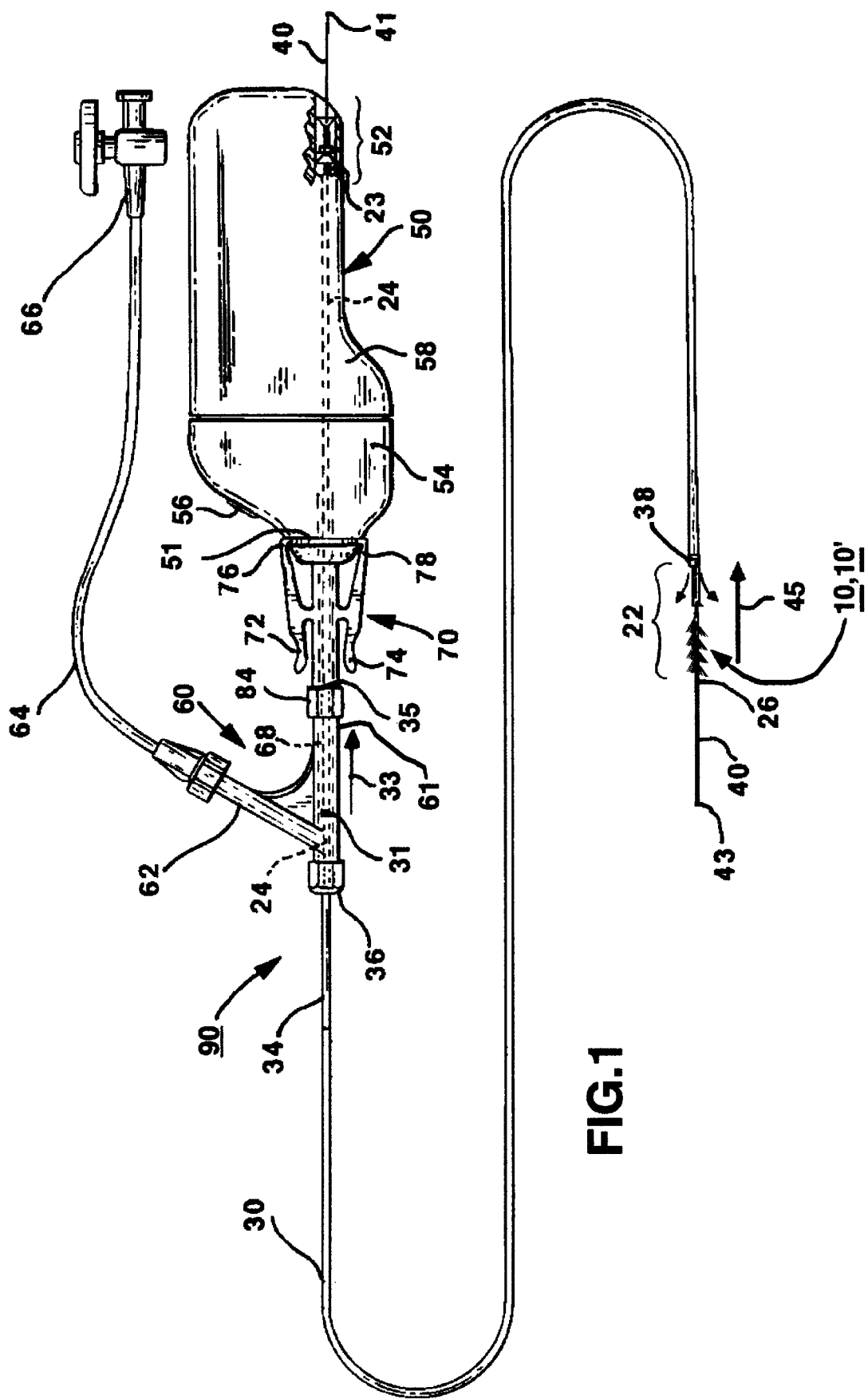
FIG. 1 is a plan view of a preferred embodiment of the brush sub-assembly and drive motor unit of the present invention coupled together as a brush and drive motor assembly.

FIG. 1 illustrates the assembly of a drive motor unit 50, brush sub-assembly 90 and guidewire 40 in a manner described in further detail in the above-referenced, commonly assigned (9135400.APP) and (9135410.APP) patent applications. In FIG. 1, the brush sub-assembly 90 comprises (i.e., includes) the miniaturized brush 10' of the second embodiment of the present invention formed over a hollow lumen brush drive shaft 20 that extends through the lumens of a brush delivery catheter 30, Y-connector 60 and clip connector 70. It will be understood that the brush 10 of the first embodiment of the present invention described hereafter can be substituted for the depicted brush 10', and reference to either brush embodiment is made herein as the "brush 10, 10'".

In the brush sub-assembly 90, the proximal end of the brush delivery catheter 30 is coupled to the distal end of a Y-connector 60 so that their lumens are aligned. A side port extension 62 of Y-connector 60 provides a fluid coupling with the brush delivery catheter lumen 32 (shown in FIG. 2) via the Y-connector lumen 68. A flexible extension tube 64 extends from the side port extension 62 and terminates in an infusion port 66 for attachment to a source of dissolving agent (not shown).

The clip connector 70 is provided between the Y-connector 60 and the drive motor unit 50 having a clip connector lumen 72 through which a relatively short portion of the proximal drive shaft section 24 extends. The interaction of the clips 76 and 78 with the circular retention groove 55 allows the drive motor unit 50 to be rotated with respect to the Y-connector 60 and the brush delivery catheter 30 or vice versa.

The brush delivery catheter 30 is reinforced by a reinforcing tube 34 adjacent its proximal end. The reinforced proximal end of the brush delivery catheter 30 is attached to the distal end of the Y-connector lumen 68 through a compression cap 36. The brush delivery catheter 30 preferably may be about 65 cm to about 115 cm long and preferably has a 6 French (2.06 mm) O.D. and a lumen I.D. of about 1.73 mm.

The brush drive shaft 20 is preferably formed of thin wall tube having a 1.4 mm O.D. and a 1.0 mm drive shaft lumen I.D., the thin wall tube formed of a polyether amide coated over stainless steel wire braid. The drive shaft 20 thus has a drive shaft lumen 26 (FIGS. 2 and 5) that extends all the way from the drive shaft proximal end opening at the drive shaft proximal end 23 seated in a drive motor proximal seal assembly 52 to the distal end opening of drive shaft lumen (shown in FIGS. 2 and 5). The guidewire 40 is shown extending from its distal end 43 through the distal end opening of the drive shaft lumen 26 of drive shaft 20 all the way through the drive shaft lumen 26 and through the proximal seal assembly 52 to its proximal end 41. It will be understood that the guidewire 40 is provided for over-the-wire introduction and positioning of the brush 10 in relation to a soft obstruction in a blood vessel or a vascular access device or the like. The guidewire 40 may be withdrawn during rotation of the brush drive shaft 20, or may be left in place.

In FIG. 1, a short distal drive shaft section 22 of drive shaft 20 is shown extending out of the distal end opening of lumen 32 of the brush delivery catheter 30 at delivery catheter distal end 38 sufficiently to expose the brush bristles 12. It will be understood that the proximal drive shaft section 24 extends proximally from the distal drive shaft section 22 within the brush delivery catheter lumen 32. The proximal drive shaft section 24 continues to extend proximally through the Y-connector lumen 68, then through the clip connector lumen 72, into a schematically illustrated drive motor lumen 54 of the drive motor unit 50 and terminates at a proximal drive shaft end 23 seated within the proximal seal assembly 52. A drive hub (not shown) is mounted on the proximal drive shaft section 24 spaced distally from proximal drive shaft end 23 sufficiently to be engaged in a drive chuck (not shown) of the drive motor unit 50 when the proximal drive shaft end 23 is seated as shown in FIG. 1. A trapped O-ring is located within the compression cap 74 at the junction of the clip connector lumen 72 with the Y-connector lumen 68 and bears against the outer surface of the drive shaft 20. The O-ring seals the Y-connector lumen 68 from loss of infusate introduced into the Y-connector lumen 68 through side port extension 62.

The drive shaft 20 is trapped within the aligned brush delivery catheter lumen 32, Y-connector lumen 68 and clip connector lumen 72. The drive shaft 20 has enlarged annular distal and proximal stops 31 and 35 that are located a precise distance apart and fit within the Y-connector lumen 68 and the clip connector lumen 72, respectively. The drive shaft 20 can be advanced within brush delivery catheter lumen 32 distally until the proximal stop 35 engages against the distal end of the clip connector lumen 72 and proximally until the distal stop 31 engages against the proximal end 61 of the Y-connector lumen 68 A limited longitudinal travel sufficient to allow the brush 10, 10' to be retracted proximally and garaged within a distal section of the of the brush delivery catheter lumen 32 is thereby provided. The brush sub-assembly 90 is employed with the motor drive assembly 50, the guidewire 40 and a source of thrombolytic agent coupled with infusion port 66 to perform a thrombectomy as described below.

The drive motor unit 50 includes a battery powered drive motor, gear assembly, and a drive chuck (not shown) within housing 58 and aligned with a drive motor lumen 54 of the drive motor unit 50. The drive motor lumen 54 is schematically depicted extending in alignment with the Y-connector lumen 68 and the clip connector lumen 72. The drive motor lumen 54 terminates proximally at a proximal seal assembly 52 (shown in partial cross-section) that seals the interior of the housing 58 from blood escaping from the proximal end opening of the drive shaft lumen 26. It will be understood that drive motor unit 50 only rotates the hollow lumen drive shaft 20 and the brush 10, 10' formed about distal drive shaft section 22. The internal drive motor is turned on by depression of button 56 which closes a power switch providing battery power to the internal drive motor. In a thrombectomy application, the internal drive motor rotates the drive shaft 20 relatively slowly, on the order of about 500–3000 RPM and in a single direction.

As noted above, a thrombolytic agent is delivered into the space in Y-connector lumen 68 outside of the outer surface of the proximal drive shaft section 24. The trapped O-ring within compression cap 74 provides a rotary seal within the proximal end of the Y-connector 62 for sealing around the exterior surface of the proximal drive shaft section 24 to inhibit the back flow of thrombolytic agent or blood through the clip connector lumen 72 and into the drive motor lumen 54 and housing 58. The thrombolytic agent is forced distally through the annular space between the outer surface of the proximal drive shaft section 24 and the inner surface of the brush delivery catheter 30 until it escapes at the distal end opening thereof.

The rotation of the brush 10, 10' to separate and mix the fibrin of a soft obstruction while a thrombolytic agent is supplied to it generally follows the teachings of the above-incorporated '653 patent. The clip connector 70, the proximal seal assembly 52, the brush 10, 10' and other features of the preferred embodiments of the present invention are not disclosed in the above-incorporated '653 and '355 patents. The drive motor unit 50 and the brush sub-assembly 90, except for the brush 10 or 10', preferably take the forms disclosed in detail in the above-referenced '(9135400.APP) and '(9135410.APP) patent applications and are described in greater detail therein. In accordance with the present invention, various improvements are made in the brush 10, 10' and the manufacture thereof as exemplified by the preferred embodiments described in reference to drawings as follows.

The first embodiment of the brush 10 is shown in FIGS. 2–4 and is preferably formed of a single spiral or spiral winding 14 of brush filaments or bristles 12 that extends around the circumference of the outer surface of the drive shaft 20. The guidewire 40 is shown extending through the drive shaft lumen 26. The spiral winding 14 preferably extends for about 1 cm along the length of the distal drive shaft section 22. Proximal and distal, band shaped, radiopaque markers 80 and 82 are formed on the distal drive shaft section 22 on either side of the spiral winding 14. A further band shaped, radiopaque marker 84 is formed at the distal end of the brush delivery catheter 30.

The spiral winding 14 and brush filaments 12 are formed of a planar sheet 100 of relatively rigid material, e.g. polyimide, that is about 0.002 inches thick and is shown in FIG. 4. The sheet 100 is shaped as shown in FIG. 4 with an elongated mounting web 102 and with a plurality N (e.g. 36) of fringe elements 104 that all extend at a fringe angle α from one long side edge 106 of the mounting web 102. The N fringe elements 104 extend in parallel to one another from their attached ends along side edge 106 of the mounting web to their free ends like the teeth of a comb or the barbs of a feather. The attached ends of the N fringe elements 104 effectively form "living hinges" when a fringe element 104 is bent with respect to its attached end with the mounting web 102.

The length $W'_{web\_actual}$ of the mounting web 102 preferably exceeds the circumference of the drive shaft distal section 22 to form a spiral winding 14 of about 2.5 revolutions. A number of dimensions and angles of the pattern of the sheet 100 appear in FIG. 4, including those of a starting tab 108 and an ending tab 110 and the widths and separations of the fringe elements 104.

To assemble the brush 10, a flat surface of the mounting web 102 is spiral wound about the exterior surface of the distal drive shaft section 22 and attached thereto by use of heat shrink bands 25 and 27 that encircle their ends and/or adhesive. The mounting web 102 is wound in the spiral winding at a pitch that is related to the angle of the spiral δ along the starting tab 108 and is determined by the dimension $L''_{web}$ plus a minor spacing of the adjoining edges of the mounting web along the other long side edge or web base 112 of mounting web 102.

After attachment of the mounting web 102 in the spiral pattern, the twisting of the mounting web 102 and the innate resilience of the sheet material 100 causes the fringe elements 104 to extend outward from the tubular drive shaft 20 at spaced apart points of the spiral pattern. Each fringe element 104 extends at the acute projection angle β with respect to a reference line normal to the longitudinal axis of the brush drive shaft 20 and extended through the living hinge or the fringe element forming the brush bristle. In this way, the fringe elements form brush bristles 12 in the spiral pattern around the circumference of the brush drive shaft 20 that tracks the winding pitch of the mounting web 104. The spiral winding pitch is dependent upon the width of the mounting web 102. The length of the mounting web 102 in relation to the winding pitch and the drive shaft distal section O.D. dictates the number of spiral revolutions of the resulting brush bristles 12 of the brush 10.

FIGS. 2 and 3 also depict how the individual fringe elements 104 extend as brush bristles 12 obliquely away from the living hinge ends attached to the mounting web 102. Each brush bristle 12 extends obliquely and distally at an offset angle θ to an imaginary line drawn on the surface of the brush drive shaft distal section 22 parallel to the longitudinal axis of the drive shaft distal section 22. The offset angle θ and the projection angle β are complements and are dependent upon the winding pitch and the fringe angle α of the fringe elements 104 of FIG. 4. These angles and the length and width of the mounting band 102 and the length of the fringe elements 104 are selected to ensure that the brush bristles 12 can be folded down against the drive shaft outer wall to garage the brush bristles 12 within the brush delivery catheter lumen.

In reference to FIG. 3, the rotation of the drive shaft 20 in the clockwise direction bends the brush bristles 12 at their attached ends "with the grain" i.e., inward against the surface of the brush drive shaft section 22, when the brush bristle ends mix with thrombin. Conversely, rotation of the drive shaft 20 in the counter-clockwise direction bends the brush bristles 12 at their attached ends "against the grain" i.e., outward away from the surface of the brush drive shaft section 22, when the brush bristle ends mix with thrombin. The brush bristles 12 are more resistant to bending, i.e., are stiffer, when rotated against the grain than when rotated with the grain.

In use of this single spiral brush embodiment, the brush drive shaft and brush are advanced within an outer brush delivery catheter lumen and over a previously placed guidewire that extends through the soft obstruction. The distal portion of the brush drive shaft 20 and the brush 10 within the brush delivery catheter lumen are advanced into or through the soft obstruction and are then extended out of the brush delivery catheter lumen distal end opening. The drive shaft 20 is rotated counter-clockwise (looking at the brush 10 from its distal end in FIG. 3) by the drive motor unit 50 coupled to its proximal end. The brush bristles 12 are rotated "against the grain" direction as shown in FIG. 3, thereby extending the brush bristles 12 outward to macerate the soft obstruction, preferably while the thrombolytic agent is applied to it through the lumen 32.

The requisite dimensions of the sheet 100 depicted in FIG. 4 for a desired O. D. ($od_{brush}$), and length ($L_{brush}$) of a brush 10 about a given drive shaft O.D. ($od_{shaft}$), may be determined by selecting a further set of variables and making the following calculations. The further set of variables include: the desired projection angle β of the bristles away from the axis of the drive shaft; the space (space) between the long side edge 106 and the base 112 when the web is wound into the spiral width; the width of each fringe element 104 ($W_{fringe}$); the length of the starting tab ($W'_{tab}$); the angle of the ending tab 110 ($\mu$); the angle of the spiral (δ); and the web to fringe length factor ($W_{factor}$).

Assume the following variables are fixed:

$od_{brush} := 6 \cdot mn$
$\beta := 22.5 \cdot deg$
$od_{shaft} := 0.045 \cdot in$
$space := 0.007 \cdot in$
$L_{brush} := 1 \cdot cm$
$W_{fringe} := 0.009 \cdot in$
$W'_{tab} := 0.06 \cdot in$
$\mu := 25 \cdot deg$
$\delta := 41.48 \cdot deg$
$W_{factor} := 0.75$ Then, the dimensions may be calculated as follows:

| | |
|---|---|
| $L_{fringe} := \dfrac{od_{brush}}{2} \cdot \dfrac{1}{\cos(\beta)}$ | $L_{fringe} = 0.128 \cdot in$ |
| $\alpha := 90 \cdot deg - (\delta + \beta)$ | $\alpha = 26.02 \cdot deg$ |
| $L'_{web} := L_{fringe} \cdot W_{factor}$ | $L'_{web} = 0.096 \cdot in$ |
| $L''_{web} := \dfrac{L'_{web}}{\cos(\delta)}$ | $L''_{web} = 0.128 \cdot in$ |
| $Pitch := L''_{web} + space$ | $Pitch = 0.135 \cdot in$ |
| $W'_{web} := \dfrac{L_{brush}}{\sin(\delta)}$ | $W'_{web} = 0.594 \cdot in$ |
| $W'_{web} := \dfrac{W_{fringe}}{\cos(\alpha)}$ | $W'_{fringe} = 0.01002 \cdot in$ |
| $Qty_{fringe} := floor\left(\dfrac{W'_{web}}{W'_{fringe}}\right)$ | $Qty_{fringe} = 59$ |
| $W'_{web\_actual} := Qty_{fringe} \cdot W'_{fringe}$ | $W'_{web\_actual} = 0.591 \cdot in$ |
| $W'_{base} := W'_{web\_actual} +$ $W'_{tab} + \left(\dfrac{L'_{web}}{\tan(\mu)} - \dfrac{L'_{web}}{\tan(\delta)}\right)$ | $W'_{base} = 0.748 \cdot in$ |
| $L'_{fringe} := L_{fringe} \cdot \cos(\alpha)$ | $L'_{fringe} = 0.115 \cdot in$ |
| $Length' := L'_{fringe} + L'_{web}$ | $Length' = 0.211 \cdot in$ |
| $W_{root} := od_{shaft} \cdot \pi + 4 \cdot space$ | $W_{root} = 0169 \cdot in$ |
| $W_{tab} := W'_{tab} \cdot \sin(\delta)$ | $W_{tab} = 0.04 \cdot in$ |
| $Length_{overall} := W'_{base} \cdot \sin(\delta)$ | $Length_{overall} = 1.259 \cdot cm$ |

FIGS. 5–11 depict a second preferred embodiment of the invention. Preferably, the brush 10' of this embodiment formed along the distal drive shaft section 22 has a proximal spiral brush section 16 and a distal spiral brush section 18 as shown in FIG. 5. The brush sections 16 and 18 are formed and attached to proximal and distal portions of the distal drive shaft section 22 generally as described above with differences as described below. However, the bristles 12 of the proximal spiral brush section 16 extend outward of the rotatable drive shaft 20 in a proximal spiral winding 17 extending in a proximal winding direction and at a first pitch through at least one revolution around the circumference of the distal drive shaft section 22. The bristles 12' of the distal spiral brush section 18 extend outward of the distal drive shaft section 22 in a distal spiral winding 19 extending in a distal winding direction opposite to the proximal winding direction and at a second pitch through at least one revolution around the circumference of the distal drive shaft section 22.

The number of revolutions of the proximal and distal spiral windings 17 and 19 and the number of bristles 12 and 12' in each respective spiral brush section 16 and 18 may be the same or differ from one another. The first and second pitches may also be the same or differ from one another in degree. Moreover, the stiffness and spacing apart of the spiral brush bristles 12 and 12' may be the same or differ.

Preferably, the spiral winding 17 of the proximal spiral brush section 16 extends about 1–5 revolutions about the circumference of the distal drive shaft section 22. The spiral winding 19 of the distal spiral brush section 16 also preferably extends about 1–5 revolutions about the circumference of the distal drive shaft section 22. Moreover, the number of brush bristles 12 may be selected to be less or more than or equal to the number of brush bristles 12'. The brush bristles 12 can be more widely spaced apart than the brush bristles 12', so that the brush bristles 12 are more sparse or less dense than the brush bristles 12'. These factors can be tailored to provide a desired overall length of the brush 10' and to ensure that the proximal and distal spiral brush sections 16 and 18 have the same or differing characteristics as they rotate. For example, they can be selected so that the proximal and distal spiral brush sections 16 and 18 impart relatively low and high fluid velocities, respectively, in the distal and proximal directions, respectively, to the blood and particles of the soft obstruction.

Preferably, the proximal and distal spiral winding directions of the proximal and distal brush sections 16 and 18 are chosen so that the proximal and distal brush bristles impel fluids distally and proximally, respectively, in the manner of opposed Archimedian screws. The sets of brush bristles 12 and 12' extend generally distally in both cases, but the mounting webs are wound in opposed winding directions. The proximal brush section 16 is wound so that the brush bristles 12 are rotated "against the grain", and the distal brush section 18 is wound so that the brush bristles 12' are rotated "with the grain" when the drive shaft 20 is rotated by the motor assembly 50. FIG. 6 is an enlarged end cross-section view along lines 6—6 of the proximal brush section of FIG. 5 showing the proximal brush bristles 12 rotated "against the grain". FIG. 7 is an enlarged end view along lines 7—7 of the distal brush section of FIG. 5 showing the distal brush bristles 12' rotated "with the grain".

Figure 8:
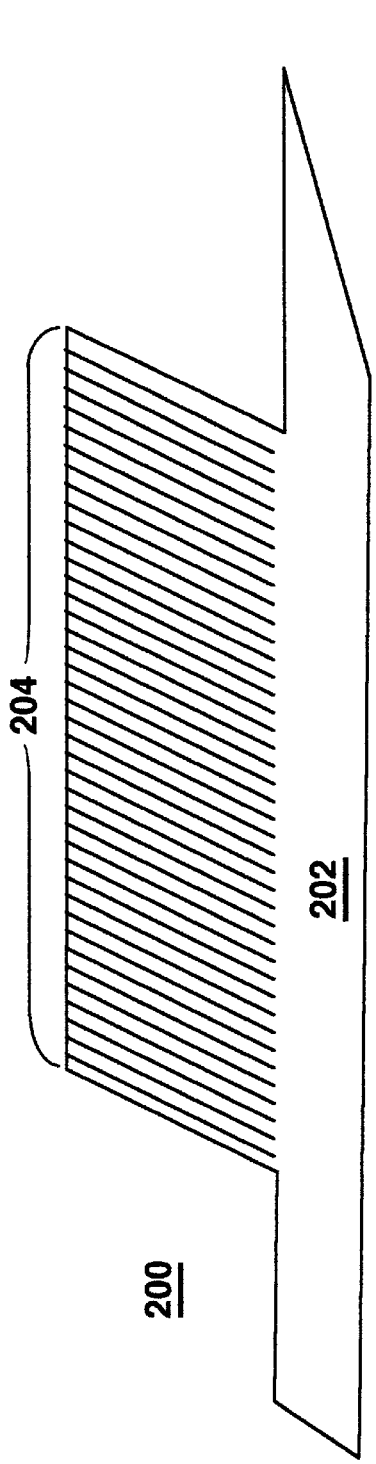
FIG. 8 is a plan view of a sheet of material cut to form an integral mounting web and a plurality of fringe elements used to form the proximal brush section of FIG. 5.

FIG. 8 is a plan view of a sheet of material 200 cut to form an integral mounting web 202 and a plurality of fringe elements 204 used to form the proximal brush section 16 when wound about a proximal portion of the distal drive shaft section 22 as shown in FIG. 5. Preferably, the fringe elements 204 are each separated apart by a spacing that is about one-half the width of each fringe element and number about 44.

Figure 9:
FIG. 9 is a plan view of a reinforcement strip employed to reinforce the mounting web of FIG. 8.
Figure 10:
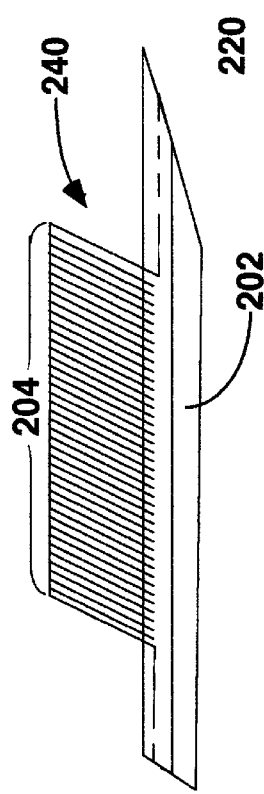
FIG. 10 is a plan view illustrating the location of the reinforcement strip of FIG. 9 over the mounting web of FIG. 8.

FIG. 9 is a plan view of a thin, polyimide, reinforcement strip 220 that is employed to reinforce the mounting web 202 of FIG. 8. The reinforcement strip 220 of FIG. 9 is adhered over the mounting web 202 of FIG. 8 using an epoxy adhesive as shown in FIG. 10. The resulting assembly 240 is wrapped about and attached to a proximal portion of the distal drive shaft section 22 in the same manner as described above with respect to the embodiment of FIG. 2.

Figure 11:
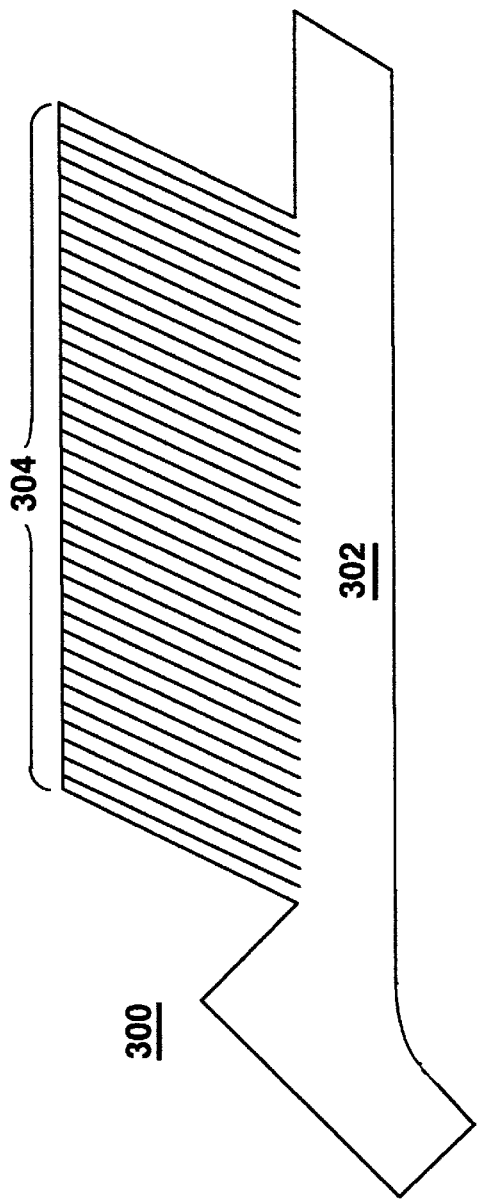
FIG. 11 is a plan view of a sheet of material cut to form an integral mounting web and a plurality of fringe elements used to form the distal brush section of FIG. 5.

Similarly, FIG. 11 is a plan view of a sheet of material 300 cut to form an integral mounting web 302 and a plurality of fringe elements 304 used to form the distal brush section 18 when wound about a distal portion of the distal drive shaft section 22 as shown in FIG. 5. Preferably, the fringe elements 304 are closely spaced together and number about 36.

Figure 12:
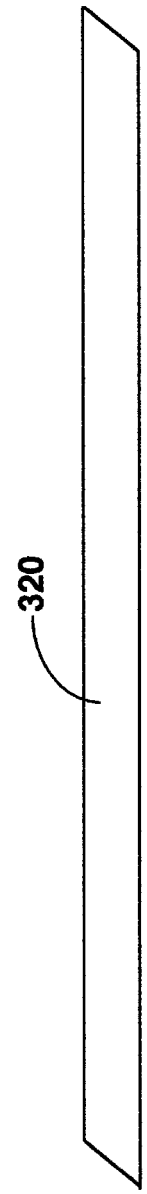
FIG. 12 is a plan view of a reinforcement strip employed to reinforce the mounting web of FIG. 11.
Figure 13:
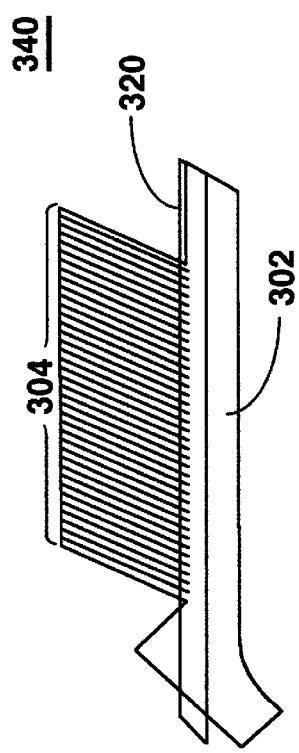
FIG. 13 is a plan view illustrating the location of the reinforcement strip of FIG. 12 over the mounting web of FIG. 11.

FIG. 12 is a plan view of a thin, polyimide, reinforcement strip 320 that is employed to reinforce the mounting web 302 of FIG. 11. The reinforcement strip 320 of FIG. 12 is adhered over the mounting web 202 of FIG. 11 using an epoxy adhesive as shown in FIG. 13. The resulting assembly 340 is wrapped about and attached to the distal portion of the distal drive shaft section 22 in the same manner as described above with respect to the embodiment of FIGS. 2–4.

Returning to the use of the thrombolytic brush sub-assembly 90, a percutaneous access is provided into an occluded medical implant vessel or into vasculature leading to an occluded native blood vessel or vascular implant in a conventional manner as disclosed in the above-incorporated '653 patent, for example. The guidewire 40 is advanced through the access device and the vasculature or directly into the accessed medical implant until its distal end passes through the soft obstruction in the lumen thereof. The proximal end of the guidewire 40 extends proximally from the vasculature access device extending through the skin. Then, it is possible to advance the brush sub-assembly 90 over the guidewire 40 while the distal brush 10 or 10' is garaged within the distal section of the brush delivery catheter lumen 32. The advancement of the distal ends of the brush delivery catheter 30 and the drive shaft 20 can be monitored by observing the radiopaque markers 80, 82 and 84 using fluoroscopy. When the site of the soft obstruction is reached, advancement over the guidewire 40 is halted, and the brush 10, 10' is advanced out of the outer brush delivery catheter lumen 32 within the soft obstruction. The brush 10, 10' is rotated as the thrombolytic agent is dispensed to dissolve the macerated fibrin and fragments of the soft obstruction.

In the preferred embodiment using the motor apparatus of FIG. 1, the brush sub-assembly 90 is advanced, while the distal brush 10 or 10' is garaged, over the guidewire 40 to the soft obstruction. In the garaged state, the stop 31 is moved proximally in the direction of arrow 33 in Y-connector lumen 68 until the stop 31 engages the proximal Y-connector lumen end 61. The distal shaft section 22 is moved proximally in the direction of arrow 45 at the same time. The brush bristles 12 are folded down "with the grain" against the distal drive shaft section 22 and the surrounding catheter lumen inner wall as they are garaged in the distal section of the brush delivery catheter lumen.

After the soft obstruction is reached, the proximal end of the guidewire 40 is inserted into the distal end opening of the drive motor lumen 54. The drive motor unit 50 is advanced over the proximal end of the guidewire 40 until the guidewire 40 extends proximally from the proximal seal assembly 52 as shown in FIG. 1. At this point, the proximal drive shaft end 23 is inserted into the distal opening of the drive shaft lumen 54. The drive motor unit 50 and the clip assembly 70 are brought together, causing the proximal drive shaft end 23 to traverse the drive shaft lumen 54 proximally and approach the proximal seal assembly 52. During the approach, the clips 76 and 78 spread apart as their free ends bear against and then ride up on the generally conical exterior surface of the housing 58. When the free ends snap into the annular retention groove 55, a number of operations and completed and connections are made. Simultaneously, the proximal drive shaft end 23 is seated into the proximal seal assembly 52, an enlarged shaft hub (not shown) of drive shaft 20 engages a drive chuck (not shown) within housing 58, and the brush 10, 10' is advanced distally out of the distal section of the brush delivery catheter lumen until a proximal stop 35 on the drive shaft proximal section 24 contacts the distal end of clip lumen 72.

When assembly is complete as shown in FIG. 1, the brush sub-assembly 90 and the drive motor unit 50 can be rotated with respect to one another by the rotation of the clip connector 70 to orientations that facilitate the infusion and manual manipulation of the assembly by the physician. Then, the drive motor unit switch 56 is closed to energize the drive motor. The brush 10, 10' is rotated through rotation of the drive shaft 20 by the proximal drive motor unit 50 in the prescribed rotation direction for macerating the soft obstruction. At the same time, a thrombolytic agent is applied through the Y-connector 60 and through the brush delivery catheter lumen 32 to the region of the brush 10, 10'. The rotation of the spiral wound brush bristles 12 causes the brush 10, 10' to macerate the soft obstruction and to impart a rotational velocity to the fragments. In such clinical use, the brush 10, 10' is rotated at a speed and direction that effects a pumping action in the blood that maintains the soft obstruction fragments in contact with the delivered thrombolytic agent rather than moving the mixture distally away from the brush 10, 10'.

In the practice of the second preferred embodiment, the brush 10' is advanced out of the brush delivery catheter lumen 32 and positioned in relation to a soft obstruction as described above. The brush 10' is rotated through rotation of the drive shaft 20 by the proximal drive motor unit 50 in a prescribed rotation direction, e.g. clockwise when viewed axially from the distal end. The proximal and distal winding directions of the proximal and distal brush sections 16 and 18 impel fluid and particles toward one another in opposite directions. In this embodiment, the rotation direction and the proximal and distal winding of the spiral windings 17 and 19 are selected to impel fluids distally and proximally, respectively, so that the soft obstruction is macerated into particles that are trapped by the opposed fluid flow between the proximal and distal spiral brush sections 16 and 18.

The brush bristles 12 formed as described above are very thin in cross-section and can readily be retracted into a small diameter lumen 32 of the outer brush delivery catheter 30 during advancement of the brush 10, 10' to a desired site and spring back to their angles of extension when released from the constraint of the outer brush delivery catheter.

In all embodiments and variations, the brush filaments may be trimmed to an even length or an uneven length in a desired pattern to provide flexible bristles extending outward from the drive shaft distal end. The resulting brush bristles 12, 12' are sufficiently resilient and thin to facilitate their folding "with the grain" into the annular space between the surface of the drive shaft distal section 22 and the surrounding surface of the brush delivery catheter lumen 32 when the brush 10, 10' is garaged. The brush bristles 12, 12' spring back to their unrestrained shape to effectively mix into the fibrin of the soft obstruction yet not damage the vessel wall.

In any of the embodiments described above, the apparatus may be modified to allow infusate to be delivered down the drive shaft lumen 26 as disclosed in certain embodiments of the above-incorporated '653 patent. The distal drive shaft section 22 may be pre-formed with weep holes or perforations to allow the dispersion of dissolving agents or other fluids introduced down the lumen while the guidewire 40 is present or after it is withdrawn. The drive shaft lumen distal end opening may be provided with self sealing flaps to seal about the guidewire 40 while the brush 10, 10' is advanced or to seal the lumen end opening after the guidewire 40 is retracted. This ensures that the introduced fluid is dispersed within or proximal to the brush bristles 12, 12'. The drive shaft lumen distal end opening may alternatively be left open to provide a fluid dispersion or flush operation distal to the brush 10, 10'. These and other features of and methods of use of the brush and drive motor unit described in the above-incorporated '653 and '355 patents may be employed in the use of the miniaturized brush 10, 10' of the present invention.

The manner of manufacture of the miniaturized brush 10, 10' of the present invention provides reduced overall outer diameter that enables its introduction through small diameter brush delivery catheter and/or blood vessel lumens. In addition, the thin wall construction provides a drive shaft lumen 26 with a relatively enlarged inner diameter for introduction over a guidewire that may be 0.035 inches in diameter, for example, and for introduction and passage of fluids therethrough. The drive shaft 20 in each assembly is reinforced sufficiently to allow advancement through tortuous blood vessel passageways and to provide torque transfer to the distal brush 10, 10'.

The brush 10, 10' of the present invention are also relatively easy to fabricate and attach to the distal drive shaft section and to tailor for specific applications. The characteristics of operation of the brush can be selected by appropriately dimensioning the fringe elements and mounting web. These dimensions may be selected to determine the number of brush bristles, the spacing between adjacent brush bristles, the pitch of the spiral winding and the number of revolutions of the spiral winding and the overall length of the brush.

In the preferred embodiment of the invention, no further apparatus is employed or steps taken to dissolve the soft obstruction or thrombus in situ. It is expected that the treatment will be commenced within hours of the onset of diagnosis, and the thrombus will be dissolved by the brushing action continually exposing the fibrin of the obstruction to the dissolving agent. To the extent that fragments are created, the agent should dissolve them before they are swept away by blood flow.

In order to contain released fragments so that the dissolving agent may complete dissolution, the brush may be introduced through the soft obstruction downstream and rotated as the brush is slowly retracted through the obstruction. Optionally, a balloon catheter or a mesh basket may be coaxially introduced through the drive shaft lumen and placed downstream to temporarily obstruct the blood and dissolving agent flow away from the site and restrain fragments to allow the concentrated dissolving agent to complete the dissolution thereof.

Advantageously, blood clots and thrombi are more readily dissolved by the mixing action of the brush bristles as the dissolving agent is introduced. Intimal hyperplasia and the risk of vessel wall rupture or pseudo-aneurysm is decreased by use of the soft brush bristles. The speed of dissolution may be reduced to minutes, in comparison with hours for introduction of the dissolving agent alone. The reduced amount of dissolving agent introduced decreases the risk of internal bleeding. Patient comfort is increased and cost of the intensive care treatment is reduced by the shortened time and reduction of exposure to the dissolving agent.

While the invention is preferably used in the above-described medical procedures, it will be recognized that a miniaturized, hollow lumen brush may have other important medical applications in body lumens. For example, medical brushes that are employed for specimen collection from various body lumens including blood vessels and other vessels, openings, tracts, cavities or ducts, e.g., cytology brushes, may be formed in the manner of forming the brush 10, 10' described above. Such medical brushes need not be motor driven or capable of being introduced over a guidewire or the like. In this regard, although the preferred embodiments of the improved brush 10, 10' described above are formed on a distal section of a hollow drive shaft 20, it will be understood that the same techniques may be used to form such brush 10, 10' on the distal ends of solid core, rotatable drive shaft.

Although particular embodiments of the invention have been described herein in some detail, this has been done for the purpose of providing a written description of the invention in an enabling manner and to form a basis for establishing equivalents to structure and method steps not specifically described or listed. It is contemplated by the inventors that the scope of the limitations of the following claims encompasses the described embodiments and equivalents thereto now known and coming into existence during the term of the patent. Thus, it is expected that various changes, alterations, or modifications may be made to the invention as described herein without departing from the spirit and scope of the invention as defined by the appended claims.

What is claimed is:

1. A miniaturized medical brush for use in a body lumen comprising:

an elongated, brush drive shaft having a shaft axis and extending between a proximal drive shaft end and a distal drive shaft end, the brush drive shaft having a proximal drive shaft section and a distal drive shaft section adjacent the distal drive shaft end having a shaft outer surface and shaft circumference, the brush drive shaft adapted to be rotated from the proximal drive shaft end about the shaft axis; and a brush comprising:

a proximal spiral winding of proximal brush bristles extending around the outer surface circumference of the distal drive shaft section and outward from the shaft surface at a projection angle to the shaft surface, the spiral winding of proximal brush bristles formed by a first planar sheet of thin, rigid material that is shaped into a first elongated, planar mounting web having a first web length and a first web width between a side edge and a base with a plurality of first fringe elements extending at a first fringe angle from the side edge of the first mounting web;

means for mounting the first mounting web mounted to the outer surface circumference of the distal drive section in a first spiral path enabling the fringe elements to extend outwardly from the spiral path to form proximal brush bristles which impel fluids in a distal direction when the brush drive shaft is rotated about the shaft axis in a first direction;

a distal spiral winding of distal brush bristles extending around the outer surface circumference of the distal drive shaft section and extending outward from the shaft surface at a projection angle thereto, the distal spiral winding of distal brush bristles formed by a second planar sheet of thin, rigid material that is shaped into a second elongated, planar mounting web having a second web length and a second web width between a side edge and a base with a plurality of fringe elements extending at a fringe angle from the side edge of the second mounting web; and means for mounting the second mounting web to the outer surface circumference of the distal drive section in a second spiral path enabling the fringe elements to extend outwardly from the spiral path to form the brush bristles which impel fluids in a proximal direction when the brush drive shaft is rotated about the shaft axis in said first direction.

2. The miniaturized brush of claim 1, wherein the brush drive shaft is adapted to be rotated at the proximal shaft end to rotate the spiral windings of proximal and distal brush bristles.

3. The miniaturized brush of claim 2, wherein the drive shaft comprises a hollow tube for allowing advancement of a guidewire therethrough.

4. The miniaturized brush of claim 3, wherein the proximal brush bristles each extend at a proximal oblique offset angle away from the longitudinal axis of the drive shaft in the distal shaft section, and the distal brush bristles each extend at a distal oblique offset angle away from the longitudinal axis of the drive shaft in the distal shaft section.

5. The miniaturized brush of claim 4, wherein said first and second mounting webs are spiral wound about proximal and distal portions of the outer surface of the distal shaft section with the proximal and distal fringe elements extending generally distally.

6. The miniaturized brush of claim 3, wherein said first and second mounting webs are spiral wound about proximal and distal portions of the outer surface of the distal shaft section with the proximal and distal fringe elements extending generally distally.

7. The miniaturized brush of claim 2, wherein said first and second mounting webs are spiral wound about proximal and distal portions of the outer surface of the distal shaft section with the proximal and distal fringe elements extending generally distally.

8. The miniaturized brush of claim 7, wherein the proximal brush bristles each extend at a proximal oblique offset angle away from the longitudinal axis of the drive shaft in the distal shaft section, and the distal brush bristles each extend at a distal oblique offset angle away from the longitudinal axis of the drive shaft in the distal shaft section.

9. The miniaturized brush of claim 1, wherein said first and second mounting webs are spiral wound about proximal and distal portions of the outer surface of the distal shaft section with the proximal and distal fringe elements extending generally distally.

10. The miniaturized brush of claim 9, wherein the proximal brush bristles each extend at a proximal oblique offset angle away from the longitudinal axis of the drive shaft in the distal shaft section, and the distal brush bristles each extend at a distal oblique offset angle away from the longitudinal axis of the drive shaft in the distal shaft section.

11. The miniaturized brush of claim 1, wherein the proximal brush bristles each extend at a proximal oblique offset angle away from the longitudinal axis of the drive shaft in the distal shaft section, and the distal brush bristles each extend at a distal oblique offset angle away from the longitudinal axis of the drive shaft in the distal shaft section.

12. The miniaturized brush of claim 11, wherein the rotation of the brush drive shaft in one direction causes the brush bristles to bend inward at their attached ends and toward the outer surface of the distal shaft section upon contact of the brush bristle free ends with a body lumen structure or material and the rotation of the brush drive shaft in the opposite direction causes the brush bristles to bend outward at their attached ends and away from the outer surface of the distal shaft section upon contact of the brush bristle free ends with a body lumen structure or material.

13. The miniaturized brush of claim 11, wherein the rotation of the brush drive shaft in one direction causes the proximal brush bristles to bend outward from the surface of said distal brush shaft section upon contact of the brush bristle free ends with a body lumen structure or material and the distal brush bristles to bend inward toward the surface of said distal brush shaft section upon contact of the brush bristle free ends with a body lumen structure or material.

14. The miniaturized brush of claim 1, wherein the rotation of the brush drive shaft in one direction causes the proximal brush bristles to bend outward from the surface of said distal brush shaft section upon contact of the brush bristle free ends with a body lumen structure or material and the distal brush bristles to bend inward toward the surface of said distal brush shaft section upon contact of the brush bristle free ends with a body lumen structure or material.

15. A method of performing a thrombectomy to dissolve a soft obstruction in a blood vessel lumen or the lumen of a medical implant coupled with the vascular system comprising the steps of:

introducing a compound brush formed about a distal shaft section of a a brush shaft having a proximal shaft section and said distal shaft section into said soft obstruction, said compound bush formed of a proximal brush section of proximal brush bristles arranged in a proximal spiral pattern in a proximal portion of said distal brush shaft section which impel fluids in a distal direction when the brush drive shaft is rotated about the shaft axis in a first direction and a distal brush section of distal brush bristles arranged in a distal spiral pattern in a distal portion of said distal brush shaft section which impel fluids in a proximal direction when the brush drive shaft is rotated about the shaft axis in said first direction;

introducing a thrombolytic agent into said soft obstruction to dissolve it; and rotating the compound brush in a first direction within the soft obstruction to pass the proximal brush bristles through the soft obstruction for macerating and exposing the soft obstruction and mixing the thrombolytic agent with the exposed soft obstruction while impelling the mixture distally and to pass the distal brush bristles through the soft obstruction for macerating and exposing the soft obstruction and mixing the thrombolytic agent with the exposed soft obstruction while impelling the mixture proximally to maximize exposure of the soft obstruction to the thrombolytic agent.

16. The method of claim 15, wherein the proximal brush bristles each extend at a proximal oblique offset angle away from the longitudinal axis of the drive shaft in the distal shaft section, and the distal brush bristles each extend at a distal oblique offset angle away from the longitudinal axis of the drive shaft in the distal shaft section.

17. The method of claim 16, wherein said proximal and distal brush bristles extend generally distally.

18. The method of claim 16, wherein said proximal and distal brush bristles each extend outward of the surface of said distal brush shaft section at a projection angle thereto.

19. The method of claim 18, wherein said rotating step further comprises the steps of forcing the proximal brush bristles outward from the surface of said distal brush shaft section upon contact of the brush bristle free ends with the exposed soft obstruction and forcing the distal brush bristles inward toward the surface of said distal brush shaft section upon contact of the brush bristle free ends with the exposed soft obstruction.

20. A method of making a miniaturized medical brush comprising the steps of:

forming an elongated, rotatable, brush drive shaft having a proximal shaft end and a distal shaft end and a proximal shaft section and a distal shaft section adjacent the distal shaft end having a shaft surface circumference, the brush drive shaft adapted to be rotated from the proximal shaft end; and forming a proximal spiral winding of brush bristles extending around the outer surface circumference of the distal drive shaft section and outward from the shaft surface at an angle thereto to form proximal brush bristles which impel fluids in a distal direction when the brush drive shaft is rotated about the shaft axis by:

shaping a first planar sheet of thin, rigid material into an elongated, planar, first mounting web having a web length and a web width between a side edge and a base with a plurality of fringe elements extending at a fringe angle from the side edge of the mounting web; and mounting the first mounting web to the outer surface circumference of the distal drive section in a spiral path enabling the fringe elements to extend outwardly from the spiral path to form the proximal spiral winding of brush bristles; and forming a distal spiral winding of brush bristles extending around the outer surface circumference of the distal drive shaft section and outward from the shaft surface at an angle thereto to form distal brush bristles which impel fluids in a proximal direction when the brush drive shaft is rotated about the shaft axis by:

shaping a second planar sheet of thin, rigid material into an elongated, planar, second mounting web having a web length and a web width between a side edge and a base with a plurality of fringe elements extending at a fringe angle from the side edge of the mounting web; and mounting the second mounting web to the outer surface circumference of the distal drive section in a spiral path enabling the fringe elements to extend outwardly from the spiral path to form the distal spiral winding of brush bristles.

21. The method of claim 20, wherein the mounting steps further comprise winding the first and second mounting webs about the outer surface circumference to extend the proximal and distal brush bristles at oblique offset angles away from the longitudinal axis of the drive shaft in the distal shaft section.

22. The method of claim 20, wherein the mounting steps further comprise winding the first and second mounting webs about the outer surface circumference to extend the proximal and distal brush bristles at oblique offset angles away from the longitudinal axis of the drive shaft in the distal shaft section and extending generally distally.

23. The method of claim 20, wherein the mounting step further comprises winding the first and second mounting webs about the outer surface circumference to extend the proximal and distal brush bristles generally distally.

* * * * *